(12) United States Patent
Koyanagi et al.

(10) Patent No.: US 12,138,061 B2
(45) Date of Patent: Nov. 12, 2024

(54) PULSE DISCRIMINATION DEVICE AND ELECTROCARDIOGRAM ANALYZER

(71) Applicant: NIHON KOHDEN CORPORATION, Tokyo (JP)

(72) Inventors: Takashi Koyanagi, Tokorozawa (JP); Kazutora Iinuma, Tokorozawa (JP); Hiroshi Kubo, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 31 days.

(21) Appl. No.: 16/573,088

(22) Filed: Sep. 17, 2019

(65) Prior Publication Data
US 2020/0093391 A1    Mar. 26, 2020

(30) Foreign Application Priority Data
Sep. 25, 2018 (JP) .................................. 2018-179346

(51) Int. Cl.
*A61B 5/316*        (2021.01)
*A61B 5/00*         (2006.01)
(Continued)

(52) U.S. Cl.
CPC .......... *A61B 5/316* (2021.01); *A61B 5/02125* (2013.01); *A61B 5/7203* (2013.01);
(Continued)

(58) Field of Classification Search
CPC ....... A61B 5/316; A61B 5/318; A61B 5/7203; A61B 5/7225; A61B 5/7278; A61B 5/02125
See application file for complete search history.

(56) References Cited

U.S. PATENT DOCUMENTS 3,552,386 A    1/1971   Horth
3,814,083 A    6/1974   Fletcher
(Continued)

FOREIGN PATENT DOCUMENTS

JP    H04-501213 A    3/1992
JP    H06-154342 A    6/1994
(Continued)

OTHER PUBLICATIONS

United States Office Action dated Sep. 24, 2021 issued in U.S. Appl. No. 16/573,002.
(Continued)

*Primary Examiner* — Scott Luan
(74) *Attorney, Agent, or Firm* — Pearne & Gordon LLP

(57) ABSTRACT

A pulse discrimination device is configured to receive an electrical signal from a living body in which a functional pulse propagates at a predetermined time interval, and is configured to discriminate between the functional pulse and a noise pulse which are included in the electrical signal. The pulse discrimination device includes: a pulse detector configured to sequentially detect an electrical pulse included in the electrical signal based on variation in an intensity of the electrical signal received from the living body; and a pulse discrimination unit configured to determine whether the electrical pulse detected by the pulse detector is the functional pulse or the noise pulse based on a detection interval of the electrical pulse detected by the pulse detector and a pulse time predetermined based on the predetermined time interval.

10 Claims, 3 Drawing Sheets

(51) Int. Cl.
*A61B 5/021* (2006.01)
*A61B 5/318* (2021.01)
(52) U.S. Cl.
CPC ............ *A61B 5/318* (2021.01); *A61B 5/7225* (2013.01); *A61B 5/7278* (2013.01)

(56) References Cited

U.S. PATENT DOCUMENTS

| | | | |
|---|---|---|---|
| 3,878,832 | A | 4/1975 | Tickner et al. |
| 4,058,118 | A * | 11/1977 | Stupay ............... A61B 5/02438 |
| | | | 600/503 |
| 4,105,023 | A | 8/1978 | Marchese et al. |
| 4,215,697 | A | 8/1980 | Demetrescu |
| 4,226,245 | A | 10/1980 | Bennett, Jr. |
| 4,432,375 | A | 2/1984 | Angel et al. |
| 4,519,401 | A | 5/1985 | Ko et al. |
| 4,527,567 | A | 7/1985 | Fischler et al. |
| 4,583,553 | A | 4/1986 | Shah et al. |
| 4,585,001 | A | 4/1986 | Belt |
| 4,603,703 | A | 8/1986 | McGill et al. |
| 4,630,204 | A | 12/1986 | Mortara |
| 4,674,508 | A | 6/1987 | DeCote |
| 4,969,467 | A | 11/1990 | Callaghan et al. |
| 5,010,887 | A * | 4/1991 | Thornander ......... A61N 1/3704 |
| | | | 607/9 |
| 5,078,133 | A | 1/1992 | Heinz et al. |
| 5,123,419 | A | 6/1992 | Platt et al. |
| 5,197,467 | A | 3/1993 | Steinhaus et al. |
| 5,201,808 | A | 4/1993 | Steinhaus et al. |
| 5,217,021 | A | 6/1993 | Steinhaus et al. |
| 5,231,990 | A | 8/1993 | Gauglitz |
| 5,330,512 | A | 7/1994 | Hauck et al. |
| 5,331,966 | A | 7/1994 | Bennett et al. |
| 5,431,170 | A | 7/1995 | Mathews |
| 5,448,997 | A | 9/1995 | Kruse et al. |
| 5,575,809 | A | 11/1996 | Sasaki |
| 5,692,907 | A | 12/1997 | Glassel et al. |
| 5,697,957 | A | 12/1997 | Noren et al. |
| 5,709,213 | A | 1/1998 | Kruse et al. |
| 5,713,935 | A | 2/1998 | Prutchi et al. |
| 5,771,898 | A | 6/1998 | Marinello |
| 6,269,268 | B1 | 7/2001 | Callaghan et al. |
| 6,381,493 | B1 | 4/2002 | Stadler et al. |
| 6,456,879 | B1 | 9/2002 | Weinberg |
| 6,477,404 | B1 * | 11/2002 | Yonce ..................... A61B 5/30 |
| | | | 600/510 |
| 6,588,423 | B1 | 7/2003 | Sinderby |
| 6,615,082 | B1 | 9/2003 | Mandell |
| 6,901,286 | B1 | 5/2005 | Sinderby et al. |
| 6,962,155 | B1 | 11/2005 | Sinderby |
| 7,336,998 | B2 | 2/2008 | Yonce |
| 7,455,643 | B1 | 11/2008 | Li et al. |
| 7,460,900 | B1 | 12/2008 | Gill et al. |
| 7,570,989 | B2 | 8/2009 | Baura et al. |
| 7,610,084 | B2 | 10/2009 | Sweeney et al. |
| 7,661,427 | B2 | 2/2010 | Sinderby et al. |
| 7,706,865 | B1 | 4/2010 | Snell |
| 8,401,627 | B1 | 3/2013 | Farazi et al. |
| 8,532,774 | B1 | 9/2013 | Hedberg et al. |
| 2002/0114386 | A1 | 8/2002 | Eklof |
| 2003/0023176 | A1 | 1/2003 | Yonce et al. |
| 2003/0050671 | A1 | 3/2003 | Bradley |
| 2004/0015197 | A1 | 1/2004 | Gunderson |
| 2007/0191900 | A1 | 8/2007 | Belk et al. |
| 2007/0260153 | A1 | 11/2007 | Ghanem et al. |
| 2008/0033494 | A1 | 2/2008 | Swerdlow |
| 2011/0270347 | A1 * | 11/2011 | Frei ..................... A61B 5/4094 |
| | | | 607/45 |
| 2011/0319769 | A1 | 12/2011 | Hedberg et al. |
| 2013/0022209 | A1 | 1/2013 | Tomimori et al. |
| 2014/0155772 | A1 * | 6/2014 | Frei ..................... A61N 1/36053 |
| | | | 607/45 |
| 2015/0190068 | A1 | 7/2015 | Cole |
| 2015/0283387 | A1 | 10/2015 | Sun et al. |
| 2015/0305642 | A1 | 10/2015 | Reinke et al. |
| 2016/0095526 | A1 * | 4/2016 | Yoshimura ............ A61B 5/339 |
| | | | 600/523 |
| 2016/0206804 | A1 | 7/2016 | Holmer et al. |
| 2016/0310746 | A1 | 10/2016 | Greenhut et al. |
| 2017/0056664 | A1 | 3/2017 | Kane et al. |
| 2018/0049660 | A1 | 2/2018 | Sato |
| 2019/0175918 | A1 | 6/2019 | Grenz et al. |
| 2019/0183374 | A1 | 6/2019 | Reinke et al. |
| 2021/0267527 | A1 | 9/2021 | Reinke et al. |

FOREIGN PATENT DOCUMENTS

| | | |
|---|---|---|
| JP | 2007-504917 A | 3/2007 |
| JP | 2009-240623 A | 10/2009 |
| JP | 2016-073373 A | 5/2016 |
| JP | 2017-513681 A | 6/2017 |
| WO | 2005-027720 A2 | 3/2005 |
| WO | 2011-064894 A1 | 6/2011 |
| WO | 2017-192775 A1 | 11/2017 |

OTHER PUBLICATIONS

Japanese Office Action dated Apr. 26, 2022 issued in Japanese Patent Application No. 2018-179346.
Japanese Office Action dated Apr. 26, 2022 issued in Japanese Patent Application No. 2018-179345.
United States Office Action dated May 24, 2023 issued in U.S. Appl. No. 17/395,674.
Office Action in related U.S. Appl. No. 17/395,674 dated Apr. 26, 2024.
Office Action for U.S. Appl. No. 17/395,674 dated Aug. 29, 2024.

* cited by examiner

PULSE DISCRIMINATION DEVICE AND ELECTROCARDIOGRAM ANALYZER

CROSS-REFERENCE TO RELATED APPLICATIONS

This application is based on and claims priority under 35 USC 119 from Japanese Patent Application No. 2018-179346 filed on Sep. 25, 2018, the contents of which are incorporated herein by reference.

TECHNICAL FIELD

The presently disclosed subject matter relates to a pulse discrimination device and an electrocardiogram analyzer, and particularly to an electrocardiogram analyzer and a pulse discrimination device that receives an electrical signal from a living body in which functional pulses propagates at a predetermined time interval, and discriminates between a noise pulse which and a functional pulse which are included in the electrical signal.

BACKGROUND

In related art, there has been proposed a pulse discrimination device that discriminates between a noise pulse and a pacing pulse output from a pacing device such as a pacemaker in order to cause a heart to beat. The pulse discrimination device receives an electrical signal from a living body to which a pacing device is attached and discriminates between a pacing pulse and a noise pulse which are included in the electrical signal. For example, a pulse discrimination device is built in an electrocardiogram analyzer such as a patient monitor and an electrocardiograph, generates an electrocardiogram based on an electrical signal received from a living body, and discriminates a pacing pulse and a noise pulse which are included in the electrical signal. Thus, for example, the output timings of the pacing pulse and the noise pulse can be displayed on the electrocardiogram, and the electrocardiogram can be analyzed in detail.

Here, in general, discrimination between the pacing pulse and the noise pulse is performed by subjecting the electrical signal received from the living body to differential processing.

For example, JP-A-2009-240623 proposes a pacemaker pulse detection device that improves the detection accuracy of a pacing pulse without increasing the number of electrode portions to be used. The pacemaker pulse detection device subjects input signals from electrocardiogram electrodes to differential amplification, and thus is capable of discriminating between a pacing pulse and a noise pulse which are included in the input signal and of removing the noise pulse.

However, the electrical signal received from the living body may include a noise pulse similar to the pacing pulse, for example, a noise pulse that is input as a differential signal the same as or similarly to the pacing pulse. By merely performing differential processing on the electrical signal as in the pacemaker pulse detection device of JP-A-2009-240623, the pacing pulse and the noise pulse which are included in the electrical signal may not be discriminated with high accuracy.

The presently disclosed subject matter has been made in order to solve such a problem of the related art, and an object thereof is to provide an electrocardiogram analyzer and a pulse discrimination device that discriminates between a functional pulse and a noise pulse which are included in an electrical signal from a living body with high accuracy.

SUMMARY

A pulse discrimination device according to a first aspect of the presently disclosed subject matter is a pulse discrimination device configured to receive an electrical signal from a living body in which a functional pulse propagates at a predetermined time interval, and configured to discriminate between the functional pulse and a noise pulse which are included in the electrical signal. The pulse discrimination device includes: a pulse detector configured to sequentially detect an electrical pulse included in the electrical signal based on variation in an intensity of the electrical signal received from the living body; and a pulse discrimination unit configured to determine whether the electrical pulse detected by the pulse detector is the functional pulse or the noise pulse based on a detection interval of the electrical pulse detected by the pulse detector and a pulse time predetermined based on the predetermined time interval.

An electrocardiogram analyzer according to a second aspect of the presently disclosed subject matter includes: the above-described pulse discrimination device; an electrocardiogram generator configured to generate an electrocardiogram based on an electrical signal received from a living body; and a display configured to display the electrocardiogram generated by the electrocardiogram generator.

DESCRIPTION OF EMBODIMENTS

Hereinafter, embodiments of the presently disclosed subject matter will be described by reference to drawings.

Embodiment 1

Figure 1:
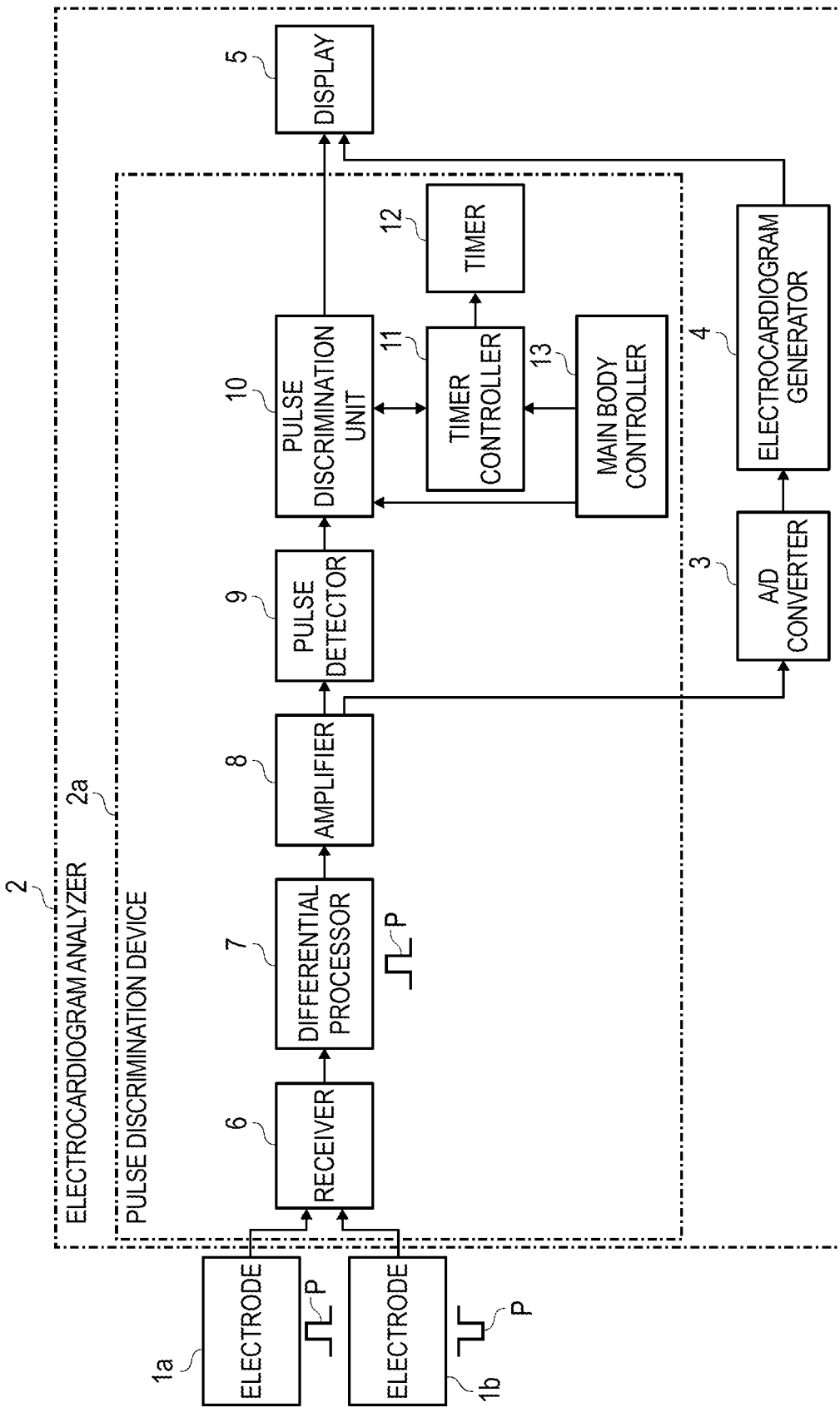
FIG. 1 is a block diagram illustrating a configuration of an electrocardiogram analyzer including a pulse discrimination device according to Embodiment 1 of the presently disclosed subject matter.

FIG. 1 illustrates a configuration of an electrocardiogram analyzer 2 that can include a pulse discrimination device according to Embodiment 1 of the presently disclosed subject matter. The electrocardiogram analyzer 2 is connected to a pair of electrodes 1a and 1b. The electrocardiogram analyzer 2 may be, for example, an electrocardiograph for electrocardiogram measurement, or may be a patient monitor capable of acquiring other vital sign parameters (respiration, body temperature, pulse rate, blood pressure, and the like). The patient monitor may be a so-called bedside monitor or a portable device such as a medical telemeter. The electrocardiogram analyzer 2 may be configured such that a display 5 can be attached and detached, or configured to transfer various data used for display.

The electrodes 1a and 1b are respectively disposed at two positions on the living body to which a pacing device is attached, and an electrical signal from the living body is input thereto. Here, the pacing device is disposed on the living body and causes a heart to beat by sequentially outputting pacing pulses (a type of functional pulse) toward the heart. Therefore, the electrical signals input into the electrodes 1a and 1b include not only a signal indicating movement of the heart, but also a pacing pulse. The electrodes 1a and 1b are arranged with respect to the pacing device such that the pacing pulses are input as differential signals P, that is, the pacing pulses input to the electrode 1a and the pacing pulses input to the electrodes 1b are input in opposite phases.

Examples of the pacing device include a pacemaker and the like.

The electrocardiogram analyzer 2 can include a pulse discrimination device 2a, an A/D converter 3, an electrocardiogram generator 4, and a display 5.

The pulse discrimination device 2a can include a receiver 6 connected to the electrodes 1a and 1b; a differential processor 7, an amplifier 8, a pulse detector 9, and a pulse discrimination unit 10 are sequentially connected to the receiver 6; and the pulse discrimination unit 10 is connected to the display 5. A timer controller 11 and a timer 12 are sequentially connected to the pulse discrimination unit 10, and a main body controller 13 is connected to the pulse discrimination unit 10 and the timer controller 11.

The receiver 6 receives the electrical signals input to the electrodes 1a and 1b, and the electrodes 1a and 1b are detachably connected thereto.

The differential processor 7 calculates a difference of the electrical signals received by the receiver 6 from the electrodes 1a and 1b, and may be configured with, for example, a differential amplifier circuit.

The amplifier 8 amplifies the intensity of the electrical signal differentiated by the differential processor 7. The amplifier 8 may be configured with, for example, an amplifier circuit.

The pulse detector 9 sequentially detects electrical pulses included in an electrical signal amplified by the amplifier 8 based on variation in an intensity of the electrical signal. Specifically, in a case where the variation in the intensity of the electrical signal exceeds a preset threshold, the pulse detector 9 detects the signal as an electrical pulse.

The timer 12 measure a detection interval of the electrical pulses detected by the pulse detector 9.

The timer controller 11 controls the timer 12 based on the detection interval of the electrical pulses at the pulse detector 9. Specifically, the timer controller 11 starts measurement of the timer 12 when the pulse detector 9 detects an electrical pulse, and clears the measurement of the timer back to zero in a case where a measurement time reaches a predetermined pulse time, without requiring the pulse detector 9 to detect the next electrical pulse. Further, the timer controller 11 clears the measurement time of the timer 12 back to zero every time the pulse detector 9 detects the next electrical pulse until the measurement time of the timer 12 reaches the pulse time.

The pulse discrimination unit 10 distinguishes the electrical pulse detected by the pulse detector 9 into a pacing pulse or a noise pulse based on the detection interval of the electrical pulse detected by the pulse detector 9 and the predetermined pulse time. Specifically, the pulse discrimination unit 10 determines that the electrical pulse detected by the pulse detector 9 is the noise pulse in a case where the detection interval of the electrical pulse is shorter than the predetermined pulse time. On the other hand, the pulse discrimination unit 10 determines that the electrical pulse detected by the pulse detector 9 is the pacing pulse in a case where the detection interval of the electrical pulse is equal to or larger than the predetermined pulse time.

Here, the pulse time is preset based on an output interval of the pacing pulse output from the pacing device, and is preferably determined as a value larger than the pulse width between a rise and a fall of the pacing pulse. For example, the pulse time may be set to a value that is larger than the pulse width of the pacing pulse and smaller than a time interval at which the pacing pulse is output from the pacing device. For example, the pulse time may be set to 8 ms.

The noise pulse is a pulse different from the pacing pulse, and corresponds to, for example, an in-phase noise and a continuous pulse.

The main body controller 13 controls each unit in the pulse discrimination device 2a.

The pulse discrimination unit 10 and the main body controller 13 are configured with a CPU and an operation program for causing the CPU to perform various processing, but may also be configured with digital circuits.

The A/D converter 3 is connected to the amplifier 8, and performs analog/digital conversion on an analog electrical signal amplified by the amplifier 8 to generate a digital electrical signal.

The electrocardiogram generator 4 is connected to the A/D converter 3 and generates an electrocardiogram based on the digital electrical signal generated by the A/D converter 3.

The display 5 is connected to the electrocardiogram generator 4 and the pulse discrimination unit 10, displays the electrocardiogram generated by the electrocardiogram generator 4, and displays a pulse mark indicating detection of the pacing pulse at the position in the electrocardiogram, which is determined to be the pacing pulse by the pulse discrimination unit 10.

Figure 2:
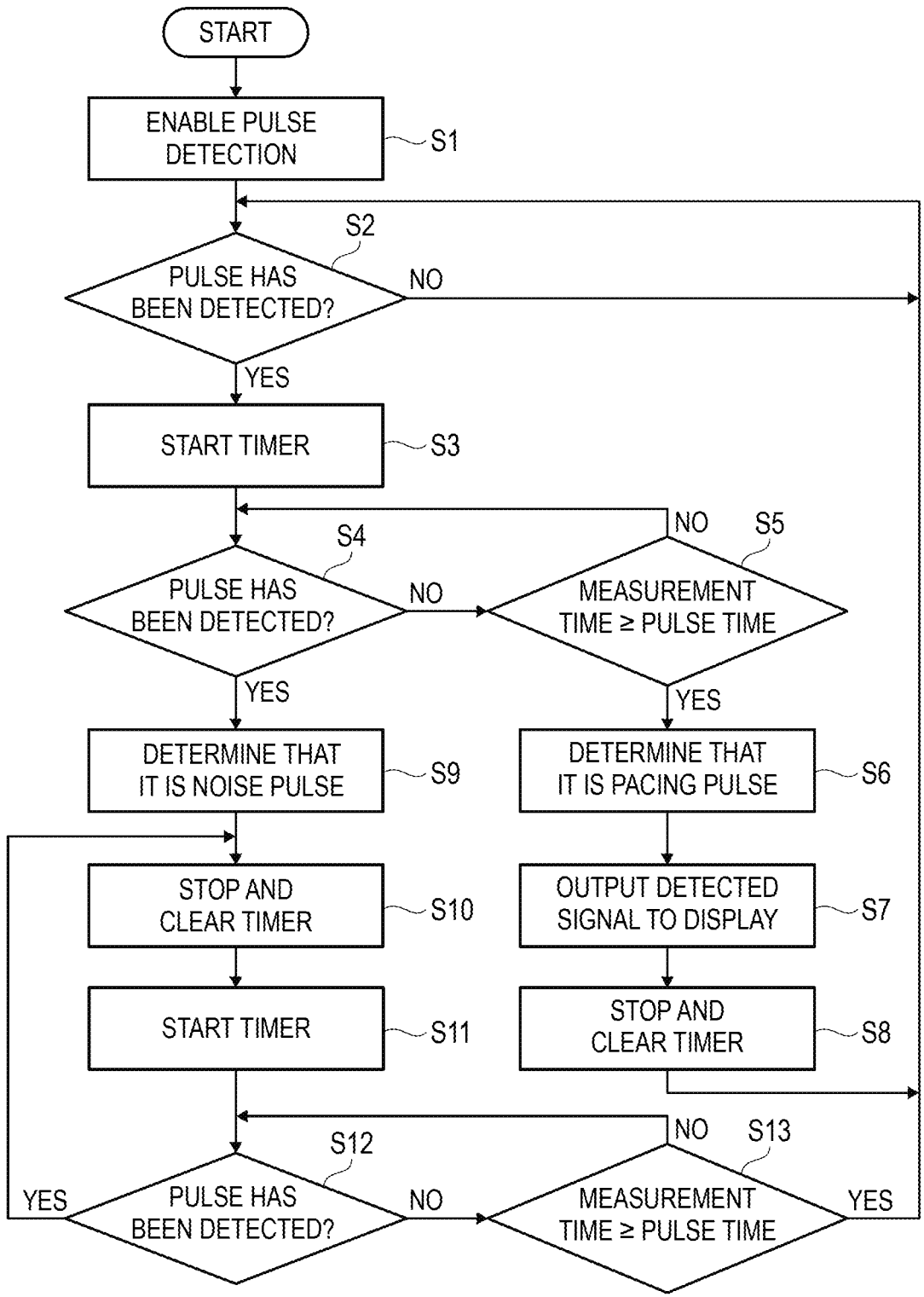
FIG. 2 is a flowchart illustrating an operation of Embodiment 1.

Next, operation of Embodiment 1 will be described with reference to the flowchart of FIG. 2.

First, the electrodes 1a and 1b illustrated in FIG. 1 are arranged at two positions on the surface of the living body, and in step S1, pulse detection by the pulse detector 9 is enabled. The pacing device (not illustrated) is attached to the living body, and the pacing pulses for causing the heart to beat are sequentially output from the pacing device toward the heart at a predetermined time interval. Therefore, an electrical signal including the pacing pulses propagates in the living body, and the electrical signal is input to the electrodes 1a and 1b. Here, the electrodes 1a and 1b are arranged at positions such that the pacing pulses are input as the differential signals P. When an electrical signal is respectively input to the electrodes 1a and 1b, the electrical signal is output from the electrodes 1a and 1b to the receiver 6 of the pulse discrimination device 2a.

When the electrical signal output from the electrodes 1a and 1b is received by the receiver 6, the receiver 6 outputs the electrical signal received from the electrodes 1a and 1b to the differential processor 7. The differential processor 7 performs differential processing of the electrical signal input from the receiver 6, that is, calculates the difference of the electrical signal received at the two different positions. Therefore, the pacing pulses and the like input as the differential signals P are increased by each other and become a large value due to the differential processing. On the other hand, electrical pulses input as in-phase signals, for example, noise pulses caused by vibration of an external device and the like, cancel each other and become a small value, for example, zero. The electrical signal obtained via the differential processing is output from the differential processor 7 to the amplifier 8 to be amplified, and then is output to the pulse detector 9.

As described above, the electrical signals input as the differential signals P can be extracted by subjecting the electrical signals input from the electrodes 1a and 1b to differential processing.

The electrical signal amplified by the amplifier 8 is also output from the amplifier 8 to the A/D converter 3.

The pulse detector 9 detects an electrical pulse included in the electrical signal input from the amplifier 8 based on the variation in the intensity of the electrical signal, and, in a case where an electrical pulse is detected, outputs a detection signal of the electrical pulse to the pulse discrimination unit 10. In step S2, the pulse discrimination unit 10 determines whether or not an electrical pulse has been detected based on the detection signal from the pulse detector 9. Specifically, in a case where the detection signal is input, the pulse discrimination unit 10 determines that an electrical pulse is detected, and starts the timer 12 via the timer controller 11 in step S3. On the other hand, in a case where no detection signal is input, the pulse discrimination unit 10 determines that no electrical pulse is detected, and repeats step S2 until a detection signal is input from the pulse detector 9.

After the timer 12 is started in step S3, the pulse detector 9 continuously detects a next electrical pulse, and the pulse discrimination unit 10 determines whether or not the next electrical pulse is detected in step S4. In a case where the pulse discrimination unit 10 determines that the next electrical pulse is not detected, the pulse discrimination unit 10 proceeds to Step S5 and determines whether or not the measurement time of the timer 12 is equal to or larger than the predetermined pulse time. At this time, the pulse time may be set to, for example, a value that is larger than the pulse width of the pacing pulse and smaller than a time interval at which the pacing pulse is output from the pacing device.

In a case where the pulse discrimination unit 10 determines that the measurement time of the timer 12 is equal to or larger than the pulse time, the pulse discrimination unit 10 determines the electrical pulses as the pacing pulses in S6, and proceeds to step S7 to output a detection signal of the pacing pulses to the display 5. Subsequently, in step S8, the pulse discrimination unit 10 stops and clears measurement of the timer 12 via the timer controller 11, and returns to step S2 to repeatedly execute detection of the electrical pulse.

On the other hand, in a case where the pulse discrimination unit 10 determines that the measurement time of the timer 12 is smaller than the pulse time in step S5, the process returns to step S4, and the pulse detector 9 determines again whether or not the next electrical pulse is detected.

In a case where the pulse discrimination unit 10 determines that the next electrical pulse is detected before the measurement time of the timer 12 reaches the pulse time in step S4, the electrical pulse is detected at an interval shorter than the pulse time, and the pulse discrimination unit 10 determines that the continuously detected electrical pulse is the noise pulse in step S9.

Here, for example, the pacing device may continuously output another electrical pulse at a short interval between outputting the pacing pulses. Since such electrical pulse is input as the differential signals P from the electrodes 1a and 1b, it is difficult to determine whether or not the electrical pulse is the pacing pulse only by differential processing.

Therefore, by whether not the electrical pulse is the noise pulse based on the output interval of the pacing pulse output from the pacing device, the pulse discrimination unit 10 can determine that the noise pulse input is the differential signals P from the electrodes 1a and 1b with high accuracy.

In this way, when the pulse discrimination unit 10 determines that the continuously detected electrical pulse is the noise pulse, the pulse discrimination unit 10 stops and clear the measurement of the timer 12 via the timer controller 11 in step S10, and proceeds to step S11 to restart the timer 12.

Subsequently, in step S12, the pulse discrimination unit 10 further determines whether or not the next electrical pulse has been detected based on the detection signal from the pulse detector 9. In a case where the pulse discrimination unit 10 determines that the next electrical pulse is not detected, the pulse discrimination unit 10 proceeds to Step S13 and determines whether or not the measurement time of the timer 12 is equal to or larger than the predetermined pulse time.

In a case where the pulse discrimination unit 10 determines that the measurement time of the timer 12 is equal to or larger than the pulse time, no noise pulse is detected, and the pulse discrimination unit 10 returns to step S2 to repeatedly execute detection of the electrical pulse. On the other hand, in a case where the pulse discrimination unit 10 determines that the measurement time of the timer 12 is smaller than the pulse time in step S13, the process returns to step S12, and the pulse detector 9 determines again whether or not the next electrical pulse is detected.

In this way, in a case where the pulse discrimination unit 10 determines that the next electrical pulse is detected before the measurement time of the timer 12 reaches the pulse time in step S12, the electrical pulse is the noise pulse, the process returns to step S10, the timer controller 11 stops and clears the timer 12, and restarts the timer in step S11. The pulse discrimination unit 10 may execute steps S10 and S11 after returning to step S9.

In this way, the timer controller 11 clears and repeatedly starts the measurement time of the timer 12 every time the pulse detector 9 detects the next electrical pulse until the measurement time of the timer 12 reaches the pulse time. Therefore, the pulse discrimination unit 10 can collectively determines that the electrical pulses continuously detected during that period are the noise pulse without missing, and can remove the electrical pulses from discrimination of the pacing pulse.

Here, the electrical signal output from the amplifier 8 to the A/D converter 3 is converted into a digital electrical signal by the A/D converter 3 and then output to the electrocardiogram generator 4. Then, the electrocardiogram generator 4 generates an electrocardiogram based on the electrical signal input from the A/D converter 3, and outputs the electrocardiogram signal to the display 5.

Figure 3:
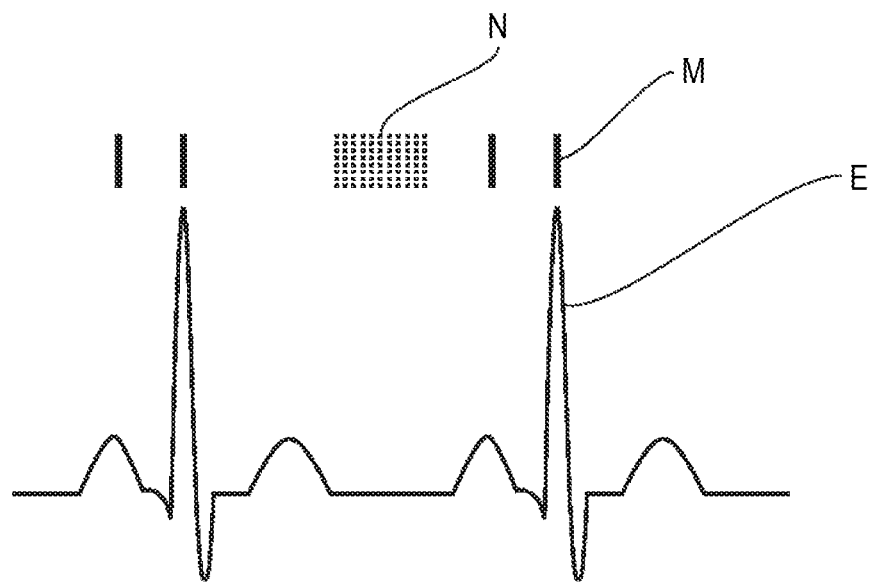
FIG. 3 is a diagram illustrating a state in which an electrocardiogram is displayed on a display.

Thereby, as illustrated in FIG. 3, an electrocardiogram E indicating beat of the heart of the living body is displayed on the display 5. In step S7, the detection signal of the pacing pulse output from the pulse discrimination unit 10 is input to the display 5. Therefore, the display 5 displays a pacing mark M indicating output of the pacing pulse from the pacing device in a manner superimposing the electrocardiogram E at a position corresponding to detection of the pacing pulse.

At this time, the pulse discrimination unit 10 discriminates the noise pulse input as the differential signals P from the electrodes 1a and 1b with high accuracy, and thus is capable of reliably preventing the noise pulse from being erroneously displayed as the pacing pulse on the display unit 5. Further, since the pulse discrimination unit 10 collectively determines that the electrical pulses continuously detected at a short interval are the noise pulse, and thus is capable of preventing the noise pulse N from being erroneously displayed as illustrated in FIG. 3, for example, in a case where another electrical pulse is continuously output between outputting the pacing pulses from the pacing device.

Discrimination information of the noise pulse discriminated by the pulse discrimination unit 10 is not limited to the use for preventing erroneous display on the display unit 5. For example, the pulse discrimination unit 10 may output the detection signal that the noise pulse is detected to the electrocardiogram generator 4. Thereby, the electrocardiogram generator 4 can generate the electrocardiogram E without influence of the noise pulse based on the detection signal.

According to the present embodiment, the pulse discrimination unit 10 determines that the electrical pulse is one of the pacing pulse and the noise pulse based on the output interval from the pacing device of the pacing pulse and the predetermined pulse time, and thus can discriminates the noise pulse input as the differential signals P from the electrodes 1a and 1b with high accuracy.

Embodiment 2

In Embodiment 1, the pulse detector 9 preferably detects the electrical pulse included in the electrical signal input from the electrodes 1a and 1b based on variation in the intensity at the rise and the fall of the electrical signal.

Figure 4:
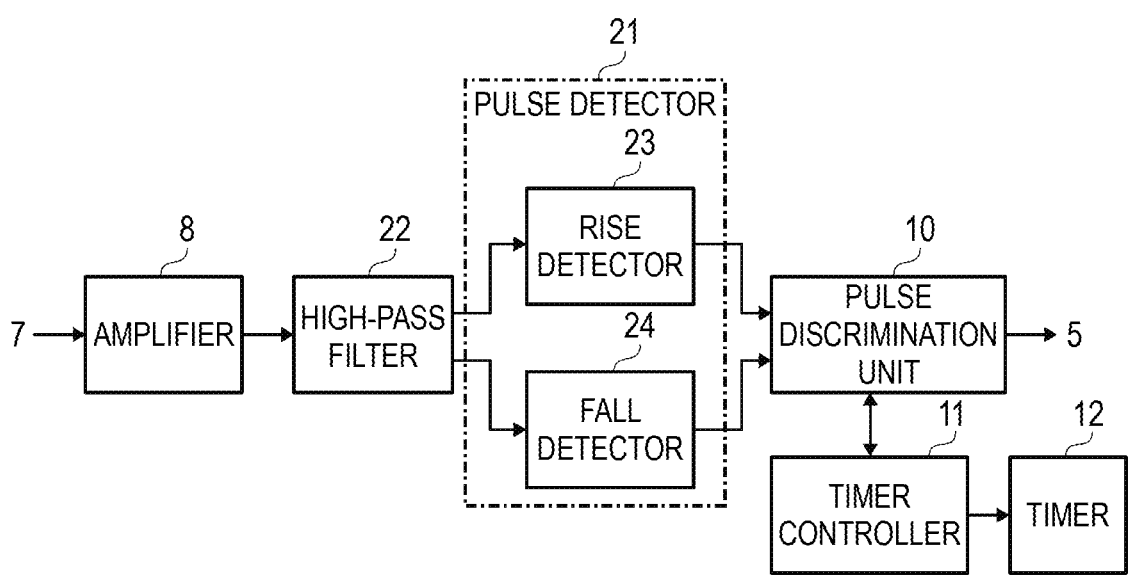
FIG. 4 is a block diagram illustrating a main part of an electrocardiogram analyzer according to Embodiment 2.

For example, as illustrated in FIG. 4, a pulse detector 21 may be disposed instead of the pulse detector 9 of Embodiment 1, and a high pass filter 22 may be newly arranged between the amplifier 8 and the pulse detector 21.

The high-pass filter 22 attenuates a component lower than a predetermined frequency among the electrical signal amplified by the amplifier 8, and extracts a component having a high frequency, that is, a rise component and a fall component.

The pulse detector 21 detects a rise and a fall of the electrical signals input from the electrodes 1a and 1b, and can include a rise detector 23 and a fall detector 24.

The rise detector 23 is connected between the high-pass filter 22 and the pulse discrimination unit 10, receives the electrical signal obtained by extracting the rise component and the fall component in the high-pass filter 22, and detects the rise based on the variation in the intensity of the electrical signal.

The fall detector 24 is connected between the high-pass filter 22 and the pulse discrimination unit 10, receives the electrical signal obtained by extracting the rise component and the fall component in the high-pass filter 22, and detects the fall based on the variation in the intensity of the electrical signal.

With such configuration, the same as or similarly to Embodiment 1, when the electrical signal from the living body is input to the high-pass filter 22 via the electrodes 1a and 1b, the receiver 6, the differential processor 7, and the amplifier 8, the high-pass filter 22 extracts the rise component and the fall component of the electrical signal, and outputs to the rise detector 23 and the fall detector 24 of the pulse detector 21, respectively.

When the electrical signal is input to the rise detector 23, the rise detector 23 detects the rise of the electrical pulse based on the variation in the intensity of the electrical signal, and outputs the detection signal to the pulse discrimination unit 10. The same or Similarly, when the electrical signal is input to the fall detector 24, the fall detector 24 detects the fall of the electrical pulse based on the variation in the intensity of the electrical signal, and outputs the detection signal to the pulse discrimination unit 10.

In this way, the pulse detector 21 detects the variation in the intensity at the rise and the fall of the electrical signal, and thus is capable of detecting the electrical pulse included in the electrical signal.

When the detection signals respectively output from the rise detector 23 and the fall detector 24 are input to the pulse discrimination unit 10, the pulse discrimination unit 10 discriminates the noise pulse included in the electrical signal the same as similarly to Embodiment 1.

At this time, the pulse discrimination unit 10 discriminates the noise pulse from the electrical pulse detected by the rise detector 23 and the fall detector 24, and thus is capable of discriminates the noise pulse included in the electrical signal with higher accuracy.

According to the present embodiment, the pulse detector 21 detects the variation in the intensity at the rise and the fall of the electrical signal, and thus is capable of detecting the electrical pulse included in the electrical signal.

In the above-described Embodiments 1 and 2, the electrodes 1a and 1b are detachably connected to the receiver 6, but are not limited thereto as long as they are electrically connected to the receiver 6. For example, the electrodes 1a and 1b may be integrally connected or wirelessly connected to the receiver 6 to the receiver 6.

Further, in the above-described Embodiments 1 and 2, the electrodes 1a and 1b are disposed at two positions on the living body, but are not limited to two as long as they are capable of receiving electrical signals from a plurality of positions of the living body.

In the above-described Embodiments 1 and 2, the pulse discrimination unit 10 determines that an electrical pulse different from the pacing pulse is the noise pulse, but it is not limited thereto as long as it can determine that an electrical pulse different from the functional pulse propagated in the living body at a predetermined time interval is the noise pulse. For example, the pulse discrimination unit 10 may receive an electrical signal from the living body in which the functional pulse propagates at the predetermined time interval via the electrodes 1a and 1b, and may determine that an electrical pulse different from the functional pulse included in the electrical signal is the noise pulse.

A pulse discrimination device according to a first aspect of the presently disclosed subject matter is a pulse discrimination device configured to receive an electrical signal from a living body in which a functional pulse propagates at a predetermined time interval, and configured to discriminate between the functional pulse and a noise pulse which are included in the electrical signal. The pulse discrimination device includes: a pulse detector configured to sequentially detect an electrical pulse included in the electrical signal based on variation in an intensity of the electrical signal received from the living body; and a pulse discrimination unit configured to determine whether the electrical pulse detected by the pulse detector is the functional pulse or the noise pulse based on a detection interval of the electrical pulse detected by the pulse detector and a pulse time predetermined based on the predetermined time interval.

Here, the pulse discrimination unit may be configured to determine that the electrical pulse detected by the pulse detector is the noise pulse, in a case where the detection interval of the electrical pulse is shorter than the pulse time.

In addition, the pulse discrimination unit may be configured to determine the electrical pulse detected by the pulse detector is the functional pulse, in a case where the detection interval of the electrical pulse is equal to or larger than the pulse time.

In addition, the pulse time may be set to a value larger than a time of the pulse width of the functional pulse.

In addition, the pulse discrimination device may further include: a timer configured to measure the detection interval of the electrical pulse; and a timer controller configured to start measurement of the timer when the electrical pulse is detected by the pulse detector, and to stop the measurement of the timer in a case where a measurement time reaches the pulse time. In a case where a next electrical pulse is detected by the pulse detector before the measurement time of the timer reaches the pulse time, the pulse discrimination unit may be configured to determine that the next electrical pulse is the noise pulse.

In addition, the timer controller may be configured to clear the measurement time of the timer every time the next electrical pulse is detected by the pulse detector until the measurement time of the timer reaches the pulse time, and the pulse discrimination unit may be configured to determine that the electrical pulse detected by the pulse detector before the measurement time of the timer reaches the pulse time is the noise pulse.

In addition, the functional pulse may include a pacing pulse that is output at the predetermined time interval from a pacing device attached to the living body in order to cause a heart to beat.

In addition, the pulse detector may be configured to detect the electrical pulse included in the electrical signal based on a rise and a fall of the electrical signal.

An electrocardiogram analyzer according to a second aspect of the presently disclosed subject matter includes: the above-described pulse discrimination device; an electrocardiogram generator configured to generate an electrocardiogram based on an electrical signal received from a living body; and a display configured to display the electrocardiogram generated by the electrocardiogram generator.

According to the presently disclosed subject matter, since the pulse discrimination unit determines that the electrical pulse detected by the pulse detector is the noise pulse in a case where the detection interval of the electrical pulse detected by the pulse detector is shorter than the pulse time, it is possible to provide an electrocardiogram analyzer and a pulse discrimination device that discriminates between a functional pulse and a noise pulse which are included in an electrical signal from a living body with high accuracy.

What is claimed is:

1. A pulse discrimination device configured to receive an electrical signal from a living body in which a functional pulse propagates, and configured to discriminate between the functional pulse and a noise pulse which are included in the electrical signal, the pulse discrimination device comprising:
at least one processor and/or electrical circuitry configured to:
sequentially detect an electrical pulse included in the electrical signal based on variation in an intensity of the electrical signal received from the living body, the electrical pulse being an electrical signal having an intensity greater than a predetermined threshold; and
determine whether the detected electrical pulse is the functional pulse or the noise pulse based on a detection interval of the detected electrical pulse and a pulse time predetermined based on an output interval of the functional pulse,
wherein the detection interval is a time interval between two consecutive electrical pulses, and
wherein the pulse time is smaller than the output interval of the functional pulse at which the functional pulse propagates.

2. The pulse discrimination device according to claim 1, wherein the at least one processor and/or electrical circuitry is configured to determine that the detected electrical pulse is the noise pulse when the detection interval of the electrical pulse is shorter than the pulse time.

3. The pulse discrimination device according to claim 1, wherein the at least one processor and/or electrical circuitry is configured to determine the detected electrical pulse is the functional pulse when the detection interval of the electrical pulse is equal to or larger than the pulse time.

4. The pulse discrimination device according to claim 1, wherein the pulse time is set to a value larger than a time of the pulse width of the functional pulse.

5. The pulse discrimination device according to claim 1, further comprising:
a timer configured to measure the detection interval of the electrical pulse; and
a timer controller configured to start measurement of the timer when the detected electrical pulse, and to stop the measurement of the timer when a measurement time reaches the pulse time,
wherein when a next electrical pulse is detected before the measurement time of the timer reaches the pulse time, at least one processor and/or electrical circuitry is configured to determine that the next electrical pulse is the noise pulse.

6. The pulse discrimination device according to claim 5, wherein the timer controller is configured to clear the measurement time of the timer every time the next electrical pulse is detected until the measurement time of the timer reaches the pulse time, and
wherein the at least one processor and/or electrical circuitry is configured to determine that the electrical pulse detected before the measurement time of the timer reaches the pulse time is the noise pulse.

7. The pulse discrimination device according to claim 1, wherein the functional pulse includes a pacing pulse that is output at the output interval of the functional pulse from a pacing device attached to the living body in order to cause a heart to beat.

8. The pulse discrimination device according to claim 1, wherein the at least one processor and/or electrical circuitry is configured to detect the electrical pulse included in the electrical signal based on a rise and a fall of the electrical signal.

9. An electrocardiogram analyzer comprising:
the pulse discrimination device according to claim 1;
an electrocardiogram generator configured to generate an electrocardiogram based on an electrical signal received from a living body; and
a display configured to display the electrocardiogram generated by the electrocardiogram generator.

10. The pulse discrimination device according to claim 1, wherein the output interval of the functional pulse is an interval between two adjacent functional pulses output sequentially.

* * * * *